United States Patent

Ito

[11] Patent Number: 5,834,478
[45] Date of Patent: Nov. 10, 1998

[54] MORPHINAN HYDROXAMIC ACID COMPOUNDS

[75] Inventor: Fumitaka Ito, New York, N.Y.

[73] Assignee: Pfizer Inc., New York, N.Y.

[21] Appl. No.: 928,953

[22] Filed: Sep. 12, 1997

[30] Foreign Application Priority Data

Sep. 16, 1996 [WO] WIPO ............... PCT/IB96/00948

[51] Int. Cl.$^6$ ............... A61K 31/485; C07D 489/02
[52] U.S. Cl. ............... 514/282; 546/44; 546/46
[58] Field of Search ............... 546/44, 46; 514/282

[56] References Cited

FOREIGN PATENT DOCUMENTS

| 0577847 | 1/1994 | European Pat. Off. |
| 0657163 | 6/1995 | European Pat. Off. |
| 0661283 | 7/1995 | European Pat. Off. |
| 0663401 | 7/1995 | European Pat. Off. |
| 9315081 | 5/1993 | WIPO |

*Primary Examiner*—Alan L. Rotman
*Assistant Examiner*—Charanjit S. Aulakh
*Attorney, Agent, or Firm*—Peter C. Richardson; Paul H. Ginsburg

[57] ABSTRACT

This invention provides a compound of the following formula:

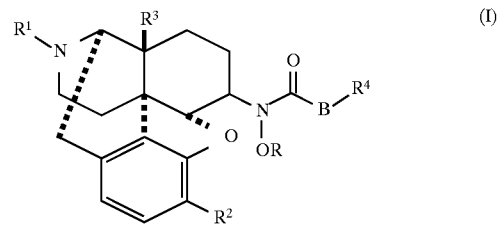

and the pharmaceutically acceptable salts thereof, wherein R is hydrogen, $C_1$–$C_5$ alkyl or an O-protecting group; B is a dircet bond, $C_1$–$C_5$ alkylene or $C_2$–$C_5$ alkenylene; $R^1$ is $C_1$–$C_5$ alkyl, $C_2$–$C_5$ alkenyl or $C_3$–$C_7$ cycloalkyl-$C_1$–$C_3$ alkyl; $R^2$ is hydroxy or $C_1$–$C_5$ alkoxy; $R^3$ is hydrogen, hydroxy or $C_1$–$C_5$ alkoxy; and $R^4$ is hydrogen, phenyl or heteroaryl selected from furyl, thienyl and pyrrolyl, the phenyl and heteroaryl being optionally substituted by one to five substitutents selected from halo, hydroxy, $C_1$–$C_3$ allyl, $C_1$–$C_3$ alkoxy and $C_2$–$C_5$ alkenyl. These compounds and pharmaceutical compositions containing such compounds are useful as analgesic, antiinflammatory, diuretic, anesthetic or neuroprotective agents, or an agent for stroke or treatment of functional bowel diseases such as abdominal pain, for the treatment of a mammalian subject, especially a human subject.

9 Claims, No Drawings

MORPHINAN HYDROXAMIC ACID COMPOUNDS

TECHNICAL FIELD

This invention relates to novel morphinan hydroxamic acid compounds and their pharmaceutically acceptable salts, and pharmaceutical compositions containing such compounds. These compounds and compositions are useful as analgesic, antiinflammatory, diuretic, anesthetic or neuroprotective agents, or an agent for treatment of stroke or functional bowel diseases such as abdominal pain, for the treatment of a mammalian subject, especially a human subject.

BACKGROUND ART

Opioid analgesics such as morphine are therapeutically useful, but their usage is strictly limited because of their side effects such as drug dependency. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as mu, delta and kappa at peripheral and central nerves in a variety of species, including human, has made a beginning towards creating new analgesics.

Recently, an opioid receptor-like ($ORL_1$) receptor was isolated and identified (Jean-Claude Meunier, et al., Nature, Vol. 377, 1995, p532–535). This receptor is a new G-protein-coupled receptor whose amino acid sequence is most closely related to those of opioid receptors. This receptor mediates inhibition of forskolin-induced accumulation of cAMP by the opiate etorphine in a stable recombinant CHO ($ORL_1$) cell line. This effect is exerted neither by the endogenous opioid peptides beta-endorphin, enkephalins and dynorphins, nor by selective mu-, delta- or kappa-opioid agonists. Thus, compounds having an antagonist activity toward the $ORL_1$ receptor as well as an agonist activity toward the mu-, delta- and/or kappa-receptors, especially kappa-receptor are expected to exhibit good analgesic activities.

International Publication No.s WO93/15081 and WO95/01178 disclose a variety of morphinan amide compounds as analgesics, diuretics or antitussives.

BRIEF DISCLOSURE OF THE INVENTION

The present invention provides a compound of the following formula:

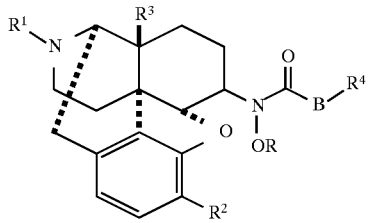

(I)

and the pharmaceutically acceptable salts or solvates thereof, wherein

R is hydrogen, $C_1$–$C_5$ alkyl or an O-protecting group;

B is a dircet bond, $C_1$–$C_5$ alkylene or $C_2$–$C_5$ alkenylene;

$R^1$ is $C_1$–$C_5$ alkyl, $C_2$–$C_5$ alkenyl or $C_3$–$C_7$ cycloalkyl-$C_1$–$C_3$ alkyl;

$R^2$ is hydroxy or $C_1$–$C_5$ alkoxy;

$R^3$ is hydrogen, hydroxy or $C_1$–$C_5$ alkoxy; and $R^4$ is hydrogen, phenyl or heteroaryl selected from furyl, thienyl and pyrrolyl, the phenyl and heteroaryl being optionally substituted by one to five substitutents selected from halo, hydroxy, $C_1$–$C_3$ alkyl, $C_1$–$C_3$ alkoxy and $C_2$–$C_5$ alkenyl.

The hydroxamic acid compounds of the present invention exhibit good binding affinity to $ORL_1$ receptor as well as significant agonist activity toward opioid receptors. Therefore the compounds of the present invention are particularly useful as an analgesic agent in mammals, especially humans. They are also useful as antiinflammatory, diuretic, anesthetic or neuroprotective agents, or an agent for treatment of stroke or functional bowel diseases such as abdominal pain, for the treatment of a mammalian subject, especially a human subject.

Accordingly, the present invention also provides a pharmaceutical composition useful as an analgesic, antiinflammatory, diuretic, anesthetic or neuroprotective agent, or an agent for treatment of stroke or functional bowel diseases such as abdominal pain, for the treatment of a mammalian subject, especially a human subject, which comprises a therapeutically effective amount of a hydroxamic acid compound of the formula (I), or its pharmaceutically acceptable salt, together with a pharmaceutically acceptable carrier.

Further, the present invention provides a method for the treatment of a medical condition for which an agonist activity toward opioid receptors and an antagonist activity toward an ORL, receptor are needed, in a mammalian subject, especially human, which comprises administering to said subject a therapeutically effective amount of a compound of the formula (I) or its pharmaceutically acceptable salt.

DETAILED DISCLOSURE OF THE INVENTION

As used herein, the term "O-protecting group" means a hydroxy protecting group to protect a hydroxy group against undesirable reactions during synthetic procedures, including but not limited to, benzyl, triphenylmethyl, tetrahydropyranyl, methoxymethyl and R'R"R'''Si wherein R',R" and R''' are each $C_1$–$C_6$ alkyl or phenyl.

Preferred compounds of this invention are those of the formula (I) wherein R is hydrogen or $C_1$–$C_5$ alkyl; B is a direct bond, $C_1$–$C_4$ alkylene or $C_2$–$C_4$ alkenylene; $R^1$ is $C_2$–$C_5$ alkenyl or $C_3$–$C_7$ cycloalkyl-$C_1$–$C_3$ alkyl; $R^2$ is hydroxy or $C_1$–$C_3$ alkoxy; $R^3$ is hydrogen, hydroxy or $C_1$–$C_3$ alkoxy; and $R^4$ is phenyl or the heteroaryl, optionally substituted by one to three substitutents selected from halo, hydroxy and $C_1$–$C_3$ alkyl.

More preferred compounds of this invention are those of the formula (I) wherein R is hydrogen or $C_1$–$C_3$ alkyl; B is a direct bond, $C_1$–$C_3$ alkylene or $C_2$–$C_3$ alkenylene; $R^1$ is $C_2$–$C_3$ alkenyl or $C_3$–$C_5$ cycloalkylmethyl; $R^2$ and $R^3$ are independently hydroxy or $C_1$–$C_3$ alkoxy; and $R^4$ is phenyl, furyl, thienyl or pyrrolyl, optionally substituted by one to three substitutents selected from halo, hydroxy and $C_1$–$C_3$ alkyl.

More preferred compounds of this invention are those of the formula (I) wherein R is hydrogen, methyl or ethyl; B is methylene, ethylene or ethenylene; $R^1$ is allyl, cyclopropylmethyl, cyclobutylmethyl or cyclopentylmethyl; $R^2$ and $R^3$ are independently hydroxy, methoxy or ethoxy; and $R^4$ is phenyl or furyl, optionally substituted by one to three substitutents selected from fluoro and chloro.

Particularly preferred compounds of this invention are those of the formula (I) wherein R is hydrogen or methyl; B is methylene or ethenylene; $R^1$ is allyl or cyclopropylmethyl; $R^2$ is hydroxy or methoxy; $R^3$ is hydroxy; and $R^4$ is 3,4-dichlorophenyl or furyl.

Preferred individual compounds of this invention are:

17-Cyclopropylmethyl-3,14β-dihydroxy-4,5α-epoxy-6α-(N-hydroxy-3,4-dichlorophenylacetamido)morphinan or its salts;

17-Cyclopropylmethyl-3,14β-dihydroxy-4,5α-epoxy-6β-(N-hydroxy-3,4-dichlorophenylacetamido)morphinan or its salts;

17-Cyclopropylmethyl-3,14β-dihydroxy-4,5α-epoxy-6α-(N-methoxy-3,4-dichlorophenylacetamido)morphinan or its salts;

17-Cyclopropylmethyl-3,14β-dihydroxy-4,5α-epoxy-6β-(N-methoxy-3,4-dichlorophenylacetamido)morphinan or its salts;

17-Cyclopropylmethyl-4,5α-epoxy-14β-hydroxy-3-methoxy-6α-(N-methoxy-3,4-dichlorophenylacetamido)morphinan or its salts;

17-Allyl-3,14β-dihydroxy-4,5α-epoxy-6α-(N-methoxy-3,4-dichlorophenylacetamido)morphinan or its salts;

17-Cyclopropylmethyl-3,14β-dihydroxy-4,5α-epoxy-6α-(N-methoxy-3,4-dichlorobenzamido)morphinan or its salts;

17-Cyclopropylmethyl-3,14β-dihydroxy-4,5α-epoxy-6α-(N-methoxy-3,4-dichlorocinnamido)morphinan or its salts; and 17-Allyl-3,14β-dihydroxy-4,5α-epoxy-6α-(N-methoxy-3-furanacrylamido)morphinan or its salts.

Particularly preferred individual compounds are 17-Cyclopropylmethyl-3,14β-dihydroxy-4,5α-epoxy-6α-(N-hydroxy-3,4-dichlorophenylacetamido)morphinan or its salts; and 17-Cyclopropylmethyl-3,14β-dihydroxy-4,5α-epoxy-6α-(N-methoxy-3,4-dichlorophenylacetamido)morphinan or its salts.

General Synthesis

The compounds of the formula (I) of this invention may be prepared as indicated in the following Preparation Methods. Otherwise stated, R, B, $R^1$, $R^2$, $R^3$ and $R^4$ are as defined above.

Method A:

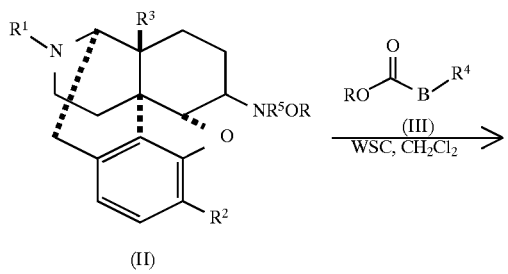

(II)

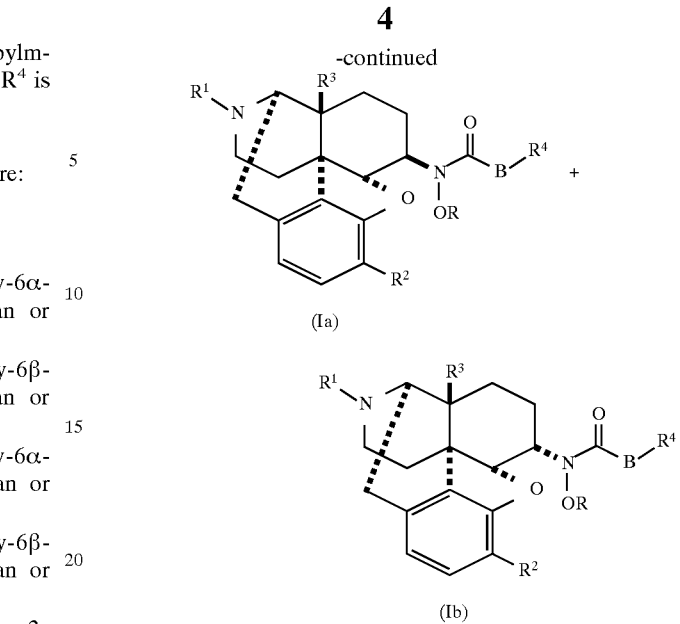

(wherein $R^5$ is hydrogen, $C_1$–$C_5$ alkyl or an O-protecting group such as t-butyldimethylsilyl (TBDMS)).

In Preparation Method A, a mixture of the morphinan hydroxamic acid compounds of the formulae (Ia) and (Ib) of the present invention may be obtained by acylation of a compound of the formula (II) (particularly $R^5$ is H) using standard acylating techniques known to those skilled in the art. For example, the compound of the formula (II) may be reacted with a carboxylic acid compound of the formula (III) ($R^4$-B—COOH) in the presence of a coupling agent in a suitable reaction inert solvent. Suitable coupling agents include dicyclohexylcarbodiimiide (DCC), water soluble carbodiimide (WSC), 2-ethoxy-N-ethoxycarbonyl-1,2-dihydroquinoline, Bop agent (Benzotriol-1-yloxy-tris(dimethylamino)phosphonium hexafluorophosphate), diethyl azodicarboxylatetriphenylphosphine, diethyl cyanophosphonate, carbonyldiimidazole and diphenylphospholyl azide. The water soluble carbodiimide is preferred. Suitable inert-reaction solvents include, for example, aromatic hydrocarbons such as benzene, toluene and xylene; ethers such as ethyl ether, dioxane and tetrahydrofuran; halogenated hydrocarbons such as chloroform, dichloromethane and dichloroethane; amides such as N,N-dimethylformamide; and nitriles such as acetonitrile. This reaction may be carried out at a temperature in the range from −30° C. to 100° C., usually from 0° C. to 30° C. The reaction takes about 30 minutes to 24 hours, usually 30 minutes to 3 hours at room temperature. The resulting products can be isolated and purified by standard techniques.

When the compound of the formula (II) wherein —NR$^5$OR is —NHOMe; and $R^2$ is OH, is used, there can be obtained the compounds of the formulae (Ia) and (Ib) wherein R is methyl; and $R^2$ is hydroxy. When the compound of the formula (II) wherein $R^2$ is —O-TBDMS, and R and $R^5$ are both TBDMS, is used, there can be obtained the compounds of the formulae (Ia) and (Ib) wherein R is TBDMS, and $R^2$ is —O-TBDMS. These TBDMS groups can be removed by a conventional method such as treatment of the resulting compound (Ia) or (Ib) with tetrabutylammonium fluoride (TBAF), to give compounds of the formula (Ia) or (Ib) wherein R and $R^2$ are OH.

The above acylation can be alternatively conducted by a reaction of the compound of the formula (II) with the other acylating agents, e.g., (1) acyl halide (e.g., $R^4$-B—COCl);

(2) anhydride (e.g., R⁴-B—CO)₂O) or a mixed anhydride in the presence of base; or (3) carboxylic ester (e.g., R⁴-B—COOR"" wherein R"" is lower alkyl) optionally in the presence of base. The conditions employed for the acylation methods can be properly chosen by the skilled persons. In addition, in the compounds of the formula (I), when R² is hydroxy, it can be convereted to alkoxy by knwon O-alkylation techniques known to the skilled persons.

The intermediate compounds of the formula (III) are known or may be prepared by known methods. The intermediate compounds of the formula (IIa) (compounds of the formula (II) wherein —NR⁵OR is —NHOMe; and R² is OH) may be prepared as shown in the following Preparation Method B-I:

Method B-I:

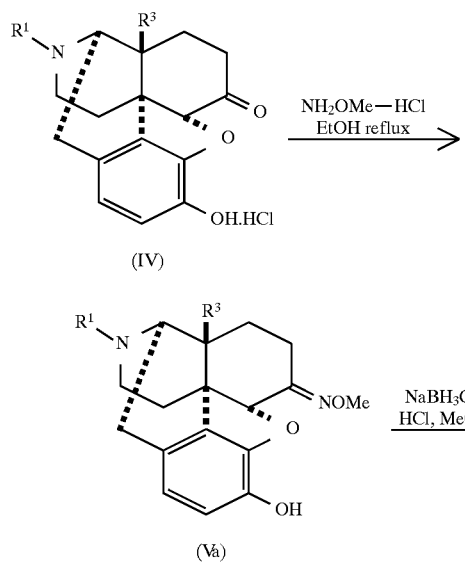

(IV)

(Va)

(IIa)

t-butyldimethylsilyl (TBDMS), and R² is —O-TBDMS) may be prepared as shown in the following Preparation Method B-II.

Method B-II:

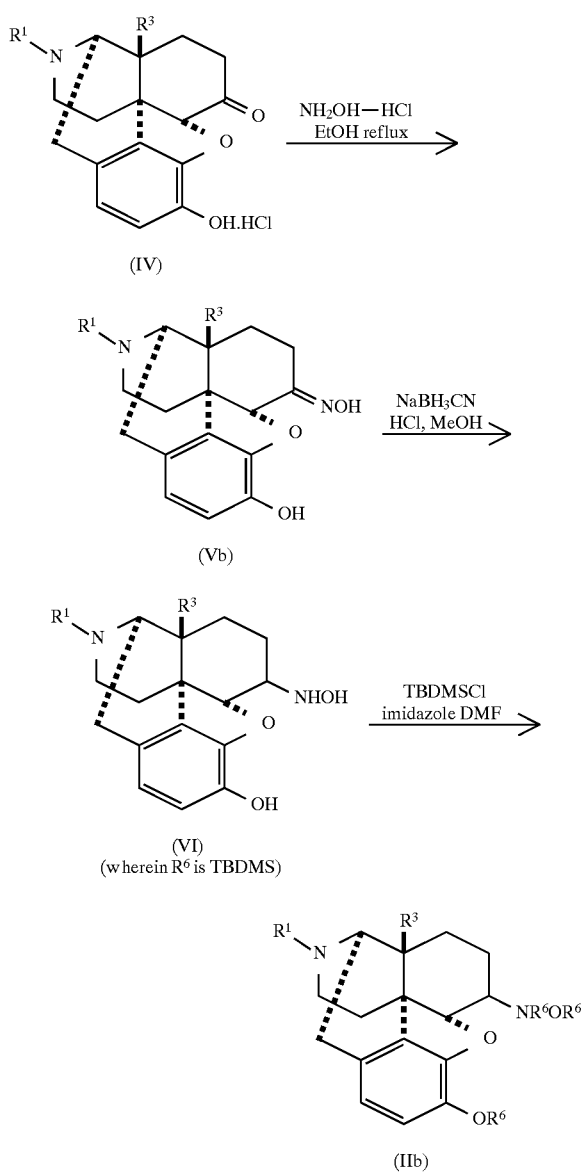

(IV)

(Vb)

(VI)
(wherein R⁶ is TBDMS)

(IIb)

As shown in the above Preparation Method B-I, firstly naltrexone hydrochloride (IV) may be reacted with O-methylhydroxylamine hydrochloride (NH₂OMe-HCl) in a suitable solvent (e.g., ethanol) to obtain a compound of the formula (Va). Naltrexone hydrochloride is a known compound and is commercially available. This reaction may be carried out at a temperature of 0° C. to 150° C. for 30 minutes to 24 hours. Preferably, this reaction may take place at reflux temperature of the solvent used for 1 to 5 hours. Secondly, the compound (Va) may be subjected to hydride-reduction with a hydride agent such as sodium cyanoborohydride (NaBH₃CN) in a suitable solvent such as methanol. The reduction may be carried out at a temperature of 0° C. to 40° C. for 30 minutes to 48 hours. Preferably, the reduction may be carried out at room temperature for 4 to 24 hours.

The intermediate compounds of the formula (IIb) (i.e., compounds of the formula (II) wherein R and R⁵ are In the above Preparation Method B-II, a compound (IIb) can be prepared by reacting naltrexone hydrochloride (IV) with hydroxylamine hydrochloride (NH₂OH—HCl) in a suitable solvent (e.g., ethanol) to obtain a compound of the formula (Vb); and further subjecting the compound (Vb) to hydride-reduction with a hydride agent (e.g., NaBH₃CN) in a suitable solvent (e.g., methanol), followed by reaction with t-butyldimethylsilyl chloride in a suitable solvent (e.g., DMF). The reaction conditions of these reactions are known to those skilled in the art (Refer to E. J. Coreyand A. Venkateswarlu, J.Am.Chem.Soc., 1972, 94, 6190; D. W. Hansen, Jr. and D. Pilipauskas, J.Org.Chem., 1985, 50, 945; and J. F. Keana, G. S. Heo, and G. T. Gaughan, J.Org.Chem., 1985, 50, 2346).

The compounds of formula (I) of this invention are usually basic, and therefore they will form acid-addition salts. All such salts are within the scope of this invention.

However, it is necessary to use an acid addition salts which are pharmaceutically-acceptable for administration to a mammal. The acid-addition salts can be prepared by standard methods, e.g., by contacting the basic and acidic compounds in substantially equivalent proportions in water or an organic solvent such as methanol or ethanol, or a mixture thereof. The salts can be isolated by evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of formula (I) of this invention wherein R is hydrogen, are acidic, and they will form base salts. All such salts are within the scope of this invention. However, it is necessary to use a base salt which is pharmaceutically-acceptable for administration to a mammal. The base salts can be prepared by standard methods, e.g., by contacting the acidic and basic compounds in substantially equivalent proportions in water or an organic solvent such as methanol or ethanol, or a mixture thereof. The salts can be isolated by evaporation of the solvent. Typical base salts which can be formed are the sodium, potassium, calcium and magnesium salts, and also salts with ammonia and amines, such as ethylamine, diethylamine, triethylamine, cyclohexylamine, piperidine and morpholine salts.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compound of the formula (I) in which $R^2$ is hydroxy groups by making an ester of the hydroxy group. Typical esters are simple alkanoate esters, such as acetate, propionate and butyrate. In addition, when $R^2$ is a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride). When the compounds of the formula (I) of this invention may form solvates such as hydrates, such solvates are included within the scope of this invention.

The compounds of the present invention of formula (I) exhibit a significant agonist activity toward opioid receptors and a good antagonist activity toward $ORL_1$ receptor, and are thus useful as analgesic, antiinflammatory, diuretic, anesthetic and neuroprotective agents, or an agent for treatment of stroke or functional bowel diseases such as abdominal pain, for the treatment of a mammalian subject, especially a human subject.

The activity of the compounds of the formula (I) of the present invention, is demonstrated by the opioid receptor and opioid like receptor binding activities. Such activity may be determined in homogenates from guinea pig whole brain, as described by Regina, A. et al. in J. Receptor Res. 12: 171–180, 1992. In summary, tissue homogenate is incubated at 25° C. for 30 min in the presence of labelled ligand and test compounds. The mu-sites are labelled by 1 nM of (3H)-[D-Ala2,MePhe4,Gly-ol5]enkephalin (DAMGO), the delta-sites by 1 nM of (3H)-[D-Pen2,5]enkephalin (DPDPE), the kappa-sites by 0.5 nM (3H)-CI977, and the $ORL_1$-sites by 1.27 nM (3H)-nociceptin. The non specific binding is measured by use of 1 $\mu$M CI977(k), 1 $\mu$M DAMGO(m), 1 $\mu$M DPDPE(d), and 100 nM nociceptin($ORL_1$). Data are expressed as the $IC_{50}$ values obtained by a non-linear fitting program using the Cheng and Prusoff equation. Some compounds prepared in the Examples showed an $IC_{50}$ value of less than 50 nM.

The analgesic activity of the compounds can also be demonstrated by the Formalin Test as described by Wheeler-Aceto, H. et al. in Psychopharmacology 104: 35–44, 1991. In this testing, male SD rats (80–100 g) are injected s.c. with a test compound dissolved in 0.1% methyl cellulose saline or vehicle. After 30 min., 50 ml of a 2% formalin are injected into a hind paw. The number of licking the injected paw per observation period is measured 15–30 min. after the injection of formalin and expressed as % inhibition compared to the respective vehicle group.

The sedation activity of the compounds can also be demonstrated by the Rotarod Test as described by Hayes, A. G. et al. in Br. J. Pharmacol. 79: 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value, defined as the dose of the drug which halves the performance time is observed in the control group.

The compounds of the formula (I) of this invention can be administered via either the oral, parenteral or topical routes to mammals. In general, these compounds are most desirably administered to humans in doses ranging from 0.01 mg to 50 mg per day, although variations will necessarily occur depending upon the weight and condition of the subject being treated, the disease state being treated and the particular route of administration chosen. However, a dosage level that is in the range of from 0.01 mg to 1 mg per kg of body weight per day, single or devided dosage is most desirably employed in humans for the treatment of pain in a postoperative patient.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparations. However, it should be understood that the invention is not limited to the specific details of these examples and preparations. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Preparation 1

Naltrexone Oxime

A suspension mixture of naltrexone hydrochloride (856 mg, 2.265 mmol) and hydroxylamine hydrochloride (236 mg, 3.4 mmol) in ethanol (10 ml) was refluxed with stirring for 4 h. After evaporation of ethanol, the resulting white solid remained was dissolved in saturated NaHCO$_3$ aqueous solution and extracted with CH$_2$Cl$_2$ (20 ml×3). The extract combined was dried (Na$_2$SO$_4$), filtered, and concentrated to give 832 mg (88.1%) of white amorphous solid. This was almost pure, so this was used for the next reaction without purification.

$^1$H NMR (270 MHz, CDCl$_3$) δ6.71 (1H, d, J=8.1Hz), 6.58 (1H, d, J=8.1Hz), 5.02 (1H, s), 3.20–3.00 (3H, m, including 1H, d, J=18.7Hz at 3.04 ppm), 2.72–2.64 (1H, m), 2.55 (1H, dd, J=6.2, 8.7Hz), 2.48–2.15 (5H, m, including 2H, d, J=6.2Hz), 1.75–1.62 (1H, m), 1.56 (1H, d, J=11.4Hz), 1.40 (1H, td, J=4.0, 13.6Hz), 0.92–0.80 (1H, m), 0.60–0.50 (2H, m), 0.17–0.10 (2H, m).

Preparation 2

17-Cyclopropylmethyl-4,5α-epoxy-3,14β-dihydroxy-6α-hydroxyaminomorphinan and 17-cyclopropylmethyl-4,5α-epoxy-3,14β-dihydroxy-6β-hydroxyaminomorphinan To a solution of naltrexone oxime (832 mg, 2.3 mmol), sodium cyanoborohydride (289 mg, 4.6 mmol), and one piece of bromocresol green in methanol (20 ml) was added a HCl gas solved methanol until the reaction mixture showed yellow color continuously. After 1.5 h stirring at room temperature, sodium cyanoborohydride (289 mg, 4.6 mmol) was added to the reaction mixture followed by addition of HCl gas solved methanol until the reaction mixture showed yellow color continuously. After 2.5 h stirring at room temperature, methanol was evaporated. The resulting residue was basified with saturated NaHCO$_3$ aqueous solution and extracted with CH$_2$Cl$_2$ (20 ml×3). The extract combined was dried (Na$_2$SO$_4$), filtered, and concentrated to give 760 mg (92.2%) of white amorphous solid. This was stereoisomer mixture(α:β=7:3) with respect to C6 assymetric center. This mixture was used for the next reaction without purification.

$^1$H NMR (270 MHz, CDCl$_3$) δ7.30–5.50 (3H, almost flat br. s), 6.70 (0.7H, d, J=8.1Hz), 6.68 (0.3H, d, J=8.1Hz), 6.55 (0.3H, d, J=8.1Hz), 6.52 (0.7H, d, J=8.1Hz), 4.99 (0.7H, d, J=3.3Hz), 4.76 (0.3H, d, J=7.3Hz), 3.70–3.60 (0.7H, m), 3.15–2.75 (2.3H, m), 2.70–2.50 (2H, m), 2.45–1.35 (9H, m), 0.90–0.75 (2H, m), 0.60–0.50 (2H, m), 0.20–0.10 (2H, m).

Preparation 3

3-t-Butyldimethylsilyloxy-6α-N,O-bis(t-butyldimethylsilyl)hydroxylamino-17-cyclopropylmethyl-4,5α-epoxy-14β-hydroxymorphinan and 3-t-butyl-dimethylsilyloxy-6β-N,O-bis(t-butyldimethylsilyl)hydroxylamino-17-cyclopropylmethyl-4,5α-epoxy-14β-hydroxymorphinan To a solution of hydroxylamine derivative (0.59 g, 1.65 mmol) and imidazole (1.12 g, 16.5 mmol) in DMF (10 ml) was added t-butylchlorodimethylsilane (1.24 g, 8.25 mmol) at room temperature. After 15 min stirring, the reaction mixture was poured into water (30 ml) and extracted with ether (20 ml×3). The extract combined was dried (Na$_2$SO$_4$), filtered, and concentrated to give 1.74 g of colorless viscous oil. This was purified by column chromatography (silica gel:200 g, CH$_2$Cl$_2$/MeOH:50/1 as eluent) to afford 165 mg of colorless viscous oil as 6α isomer (less polar) and 885 mg of 6α, 6β isomer mixture. This mixture was used for the next reaction without separation.

6α isomer:
$^1$H NMR (270 MHz, CDCl$_3$) δ6.62 (1H, d, J=8.1Hz), 6.47 (1H, d, J=8.4Hz), 4.86 (1H, br.s), 3.45–3.30 (1H,m), 3.20–3.00 (1H, m), 3.03 (1H, d, J=18.7Hz), 2.70–2.50 (2H, m), 2.40–2.20 (4H, m), 1.80–1.35 (5H, m), 0.99 (9H, s), 0.92 (9H, s), 0.92 (9H, s), 0.90–0.85 (1H, m), 0.60–0.50 (2H, m), 0.20 (3H, s), 0.17 (3H, s), 0.15–0.10(2H, m), 0.10 (12H, s).

Preparation 4

3-t-Butyldimethylsilyloxy-6α-(N-t-butyldimethylsilyloxy-3,4-dichlorophenylacetamido)-17-cyclopropylmethyl-4,5α-epoxy-14β-hydroxy-morphinan and 3-t-butyldimethylsilyloxy-6β-(N-t-butyldimethylsilyloxy-3,4-dichlorophenylacetamido)-17-cyclopropylmethyl-4,5α-epoxy-14β-hydroxymorphinan To a stirred solution of 6α, 6β isomer mixture of preparation 3 (885 mg, 1.26 mmol) and 3,4-dichlorophenylacetic acid (267 mg, 1.3 mmol) in $CH_2Cl_2$ (20 ml) was added WSC (268 mg, 1.4 mmol) at room temperature. After 1 h stirring, 3,4-dichlorophenylacetic acid (103 mg, 0.5 mmol) and WSC (110 mg, 0.57 mmol) was added to the reaction mixture. The reaction mixture was stirred at rt for 2 h. The reaction mixture was diluted with $CH_2Cl_2$ (30 ml), washed with saturated $NaHCO_3$ aqueous solution, dried ($NaSO_4$), and filtered. The filtrate was concentrated to give 1.48 g of colorless viscous oil. This oil was purified by column chromatography (silica gel:200 g, hexane/ethyl acetate: 8/1 to 4/1 as eluent) to afford 0.30 g of 6β isomer, 0.11 g of 6α, 6β isomer mixture, and 0.32 g of 6α isomer.

6α isomer: $^1$H NMR (270 MHz, $CDCl_3$) δ7.37 (1H, d, J=2.2Hz), 7.36 (1H, d, J=8.1Hz), 7.13 (1H, dd, J=2.2, 8.1Hz), 6.63 (1H, d, J=8.1Hz), 6.48 (1H, d, J=8.1Hz), 4.88 (1H, d, J=2.9Hz), 4.45–4.35 (1H, m), 3.79 (1H, d, J=16.9Hz), 3.70 (1H, d, J=16.5Hz), 3.08 (1H, d, J=6.6Hz), 3.02 (1H, d, J=19.1Hz), 2.70–2.55 (2H, m), 2.40–2.15 (4H, m), 1.90–1.45 (5H, m), 0.97 (9H, s), 0.95 (9H, s), 0.90–0.80 (1H, m), 0.60–0.50 (2H, m), 0.25 (3H, s), 0.25 (3H, s), 0.20–0.10 (2H, m), 0.18 (3H, s), 0.12 (3H, s).

IR(film): 3400, 1670 $cm^{-1}$.

6β isomer: Its $^1$H NMR spectrum was very complicated because of amide bond rotamers. Assignable peaks were only showed below.

$^1$H NMR (270 MHz, $CDCl_3$) δ7.24 (1H, d, J=8,1Hz), 6.93 (1H, br.s), 6.85 (1H, br.d, J=8.1Hz), 6.75 (0.5H, d, J=8.1Hz), 6.64 (0.5H, d, J=8.1Hz), 6.62 (0.5H, d, J=8.1Hz), 6.47 (0.5H, d, J=8.1Hz), 4.86 (1H, d, J=7.7Hz), 3.62 (2H, br.s), 1.02 (4.5H, s), 0.99 (4.5H, s), 0.98 (4.5H, s), 0.92 (4.5H, s), 0.60–0.50 (2H, m), 0.30 (1.5H, s), 0.29 (1.5H, s), 0.21 (1.5H, s), 0.20 (1.5H, s), 0.17 (1.5H, s), 0.16 (1.5H, s), 0.10 (3H, s).

IR(film): 3400, 1660 $cm^{-1}$.

EXAMPLE 1

17-Cyclopropylmethyl-3,14β-dihydroxy-4,5α-epoxy-6α-(N-hydroxy-3,4-dichlorophenylacetamido)morphinan To a solution of 6α isomer of preparation 4 (0.32 g, 0.41 mmol) in THF (1 ml) was added a 1M solution of tetrabutylammonium fluoride in THF (1 ml, 1 mmol) at room temperature. After 0.5 h stirring, the reaction solution was poured into saturated $NH_4Cl$ aqueous solution (20 ml) and extracted with ethyl acetate (20 ml×3). After dry ($Na_2SO_4$) and filtration, the filtrate was concentrated to give 392 mg of yellow solid. This was purified by preparative TLC (1 mm thick plate, developed two times with $CH_2Cl_2$/MeOH:10/1) to give 162 mg (72%) of yellow amophous solid.

$^1$H NMR (270 MHz, $CDCl_3$) δ7.40–7.25 (2H, m), 7.12 (1H, br.d, J=8.1Hz), 6.68 (1H, br.d, J=7.7Hz), 6.58–6.45 (1H, m), 5.10–4.95 (1H, m), 4.80–4.70 (1H, m), 3.91 (1H, br.d, J=15.8Hz),3.88–3.70 (1H, m), 3.25–2.88 (2H, m), 2.75–2.55 (2H, m), 2.45–2.15 (3H, m), 1.90–1.40 (7H, m), 0.90–0.75 (1H, m), 0.60–0.50 (2H, m), 0.20–0.10 (2H, m).

IR (film): 3500, 1640 $cm^{-1}$.

MS m/z: 544 ($M^+$, 13), 527(7), 340(65), 161(100).

This free amine 162 mg was treated with HCl gas solved MeOH (0.5 ml) at room temperature. Then the solvent was evaporated and the residue was solidified from ether by scraching to afford 155 mg of pale yellow powder. Anal. Calcd for $C_{28}H_{30}Cl_2N_2O.HCl.H_2O$: C,56.06; H, 5.54; N, 4.67. Found: C, 56.24; H, 5.63; N, 4.51.

EXAMPLE 2

17-Cyclopropylmethyl-3,14β-dihydroxy-4,5α-epoxy-6β-(N-hydroxy-3,4-dichlorophenylacetamido)morphinan To a solution of 6β isomer of preparation 4 (0.30 g, 0.39 mmol) in THF (1 ml) was added a 1M solution of tetrabutylammonium fluoride in THF (1 ml, 1 mmol) at room temperature. After 0.5 h stirring, the reaction solution was poured into saturated $NH_4Cl$ aqueous solution (20 ml) and extracted with ethyl acetate (20 ml×3). After dry ($Na_2SO_4$) and filtration, the filtrate was concentrated to give 279 mg of yellow amorphous solid. This was purified by preparative TLC (1 mm thick plate, developed with $CH_2Cl_2$/MeOH:10/1) to give 170 mg (79.8%) of white amophous solid.

$^1$H NMR (270 MHz, $CDCl_3$) δ7.36 (0.5H, br.d, J=1.8Hz), 7.28 (0.5H, d, J=8.1Hz), 7.27 (0.5H, d, J=8.1Hz), 7.02 (0.5H, d, J=1.8Hz), 6.90 (0.5H, dd, J=1.8, 7.3Hz), 6.87 (0.5H, d, J=7.3Hz), 6.70 (0.5H, d, J=8.1Hz), 6.69 (0.5H, d, J=8.4Hz), 6.53 (0.5H, d, J=8.1Hz), 4.98 (0.5H, d, J=6.6Hz), 4.92 (0.5H,d, J=7.7Hz), 4.25–4.10 (0.5H, m), 3.93 (0.5H, d, J=15.8Hz), 3.79 (0.5H, d, J=15.8Hz), 3.69 (0.5H, d, J=15.8Hz), 3.67–3.55 (0.5H, m), 3.48 (0.5H, d, J=15.8Hz), 3.30–2.90 (4H,m), 2.75–2.20 (4H, m), 1.80–1.05 (6H, m), 0.90–0.80 (1H, m), 0.60–0.50 (2H, m), 0.20–0.10 (2H, m).

IR(film): 3400, 3200, 1640, 1630 $cm^{-1}$.

MS m/z: 544($M^+$, 25.8), 528(1.7), 367(6.4), 327(28), 161(100).

This free amine 170 mg was treated with HCl gas solved MeOH (2 ml) at room temperature. Then the solvent was evaporated and the residue was solidified from ether/methanol by scraching to afford 119 mg of white powder, mp 235°–236°. Anal. Calcd for $C_{28}H_{30}Cl_2N_2O_5.HCl.H_2O$: C,56.06; H, 5.54; N, 4.67. Found: C, 56.41; H, 5.24; N, 4.66.

Preparation 5

6-Methoxyiminonaltrexone

A suspension mixture of naltrexone hydrochloride (4.133 g, 10.9 mmol) and O-methylhydroxylamine hydrochloride (1.25 g, 15 mmol) in ethanol (40 ml) was refluxed with stirring for 3 h. After evaporation of ethanol, the resulting white solid remained was dissolved in saturated $NaHCO_3$ aqueous solution and extracted with $CH_2Cl_2$ (100 ml×3). The extract combined was dried ($Na_2SO_4$), filtered, and concentrated to give 3.984 g (98.6%) of white amorphous solid. This was almost pure, so this was used for the next reaction without purification.

$^1$H NMR (270 MHz, $CDCl_3$) δ6.73 (1H, d, J=8.4Hz), 6.57 (1H, d, J=8.1Hz), 5.30 (1H, s), 4.98 (1H, s), 3.89 (3H, s), 3.12 (1H, d, J=6.2Hz), 3.05 (1H, d, J=18.7Hz), 2.85–2.20 (9H, m), 1.65–1.55 (2H, m), 1.40–1.25 (1H, m), 0.95–0.80 (1H, m), 0.60–0.50 (2H, m), 0.20–0.10 (2H, m).

IR(Nujol): 3200, 1640, 1615 $cm^{-1}$.

MS m/z: 371($M^+$+1, 100), 370($M^+$, 100), 339(50), 329 (66), 315(52), 273(41), 243(38), 110(80.

Preparation 6

17-Cyclopropylmethyl-3,14β-dihydroxy-4,5α-epoxy-6α-methoxyaminomorphinan and 17-cyclopropylmethyl-3,14β-dihydroxy-4,5α-epoxy-6β-methoxyaminomorphinan To a solution of 6-methoxyiminonaltrexone (3.97 g, 10.7 mmol), sodium cyanoborohydride (1.57 g, 25 mmol), and one piece of bromocresol green in methanol (40 ml) was added a HCl gas solved methanol until the reaction mixture showed yellow color continuously. After 0.5 h stirring at room temperature, sodium cyanoborohydride (1.40 g, 22 mmol) was added to the reaction mixture followed by addition of HCl gas solved methanol until the reaction mixture showed yellow color continuously. After 8 h stirring at room temperature, methanol was evaporated. The resulting residue was basified with saturated $NaHCO_3$ aqueous solution and extracted with $CH_2Cl_2$ (30 ml×3). The extract combined was dried $Na_2SO_4$), filtered, and concentrated to give 3.962 g of white amorphous solid. This was purified by column chromatography (silica gel: 100 g, $CH_2Cl_2$/MeOH:30/1 as eluent) to give 1.141 g of white amorphous solid as less polar main product (6α isomer), 1.733 g of white amorphous solid as a mixture of 6α,β isomers, and 0.650 g of white amorphous solid as more polar product(6β isomer). 1.733 g of 6α, β isomers mixture was purified again by column chromatography (silica gel: 100 g, $CH_2Cl_2$/MeOH:30/1 as eluent) to give 0.536 g of 6α isomer, 0.610 g of 6α, β isomers mixture, and 0.739 g of 6β isomer. Total yield of 6α isomer was 42.1% and 6β isomer was 34.9%.

6-α isomer:

$^1$H NMR (270 MHz, $CDCl_3$) δ6.70 (1H, d, J=8.1Hz), 6.51 (1H, d, J=8.1Hz), 4.85 (1H, d, J=3.3Hz), 3.72–3.60 (1H, m), 3.62 (3H, s), 3.10 (1H, d, J=7.0Hz), 3.04 (1H, d, J=18.7Hz), 2.70–2.60 (1H, m), 2.57 (1H, dd, J=6.6, 8.7Hz), 2.43–2.20 (4H, m), 1.80–1.35 (4H, m), 0.90–0.70 (2H, m), 0.60–0.50 (2H, m), 0.20–0.10 (2H, m).

IR(Nujol): 3350, 3250 $cm^{-1}$.

MS m/z: 372($M^+$, 100), 341(100), 323(37), 256(54), 129(52), 98(52), 73(95).

6-β isomer:

$^1$H NMR (270 MHz, $CDCl_3$) δ6.68 (1H, d, J=8.4Hz), 6.56 (1H, d, J=8.1Hz), 4.69 (1H, d, J=7.3Hz), 3.64 (3H, s), 3.07 (1H, d, J=5.5Hz), 3.01 (1H, d, J=18.3Hz), 2.75–2.60 (2H, m), 2.58 (1H, dd, J=5.9, 8.7Hz), 2.37 (2H, d, J=6.6Hz), 2.35–2.02 (3H, m), 1.80–1.60 (2H, m), 1.55–1.33 (2H, m), 0.90–0.80 (1H, m), 0.60–0.50 (2H, m), 0.20–0.10 (2H, m).

IR(Nujol): 3350, 3250 $cm^{-1}$.

MS m/z: 372($M^+$, 84), 357(5), 341(8), 327(9), 323(13), 226(38), 84(88), 55(100).

EXAMPLE 3

17-Cyclopropylmethyl-3,14β-dihydroxy-4,5α-epoxy-6α-(N-methoxy-3,4-dichlorophenylacetamido)morphinan To a stirred solution of 17-cyclopropylmethyl-4,5α-epoxy-3,14β-dihydroxy-6α-methoxyaminomorphinan (240 mg, 0.64 mmol) and 3,4-dichlorophenylacetic acid (267 mg, 1.3 mmol) in $CH_2Cl_2$ (5 ml) was added WSC (249 mg, 1.3 mmol) at room temperature. After 1 h stirring, the reaction solution was diluted with $CH_2Cl_2$ (20 ml), washed with saturated $NaHCO_3$ aqueous solution, dried ($Na_2SO_4$), and filtered. The filtrate was concentrated to give 521 mg of white amorphous solid. This was dissolved in mixed solvent ($CH_2Cl_2$/MeOH:¼, 5 ml). To this solution was added K2CO3(138 mg, 1 mmol) at room temperature. After 1 h stirring, MeOH was evaporated and the resulting residue was dissolved in water and extracted with $CH_2Cl_2$ (20 ml×2).

After dry($Na_2SO_4$) and filtration, the filtrate was concentrated to give 521 mg of colorless viscous oil, which was purified by column chromatography (silica gel: 60 g, $CH_2Cl_2$/MeOH: 20/1 as eluent) to afford 275 mg (76.8%) of white amophous solid.

$^1$H NMR (270 MHz, $CDCl_3$) δ7.44 (1H, d, J=2.2Hz), 7.39 (1H, d, J=8.4Hz), 7.17 (1H, dd, J=2.2, 8.1Hz), 6.70 (1H, d, J=8.1Hz), 6.53 (1H, d, J=8.1Hz), 4.85–4.75 (1H, m), 4.77 (1H, d, J=3.7Hz), 3.82 (1H, d, J=15.4Hz), 3.78 (3H,s), 3.73 (1H, d, J=15.4Hz), 3.10 (1H, d, J=7.0Hz), 3.03 (1H, d, J=18.7Hz), 2.67–2.55 (2H, m), 2.42–2.17 (4H, m), 1.85–1.30 (5H, m), 0.90–0.77 (1H, m), 0.57–0.49 (2H, m), 0.15–0.08 (2H, m).

IR(Nujol): 3350, 1630 $cm^{-1}$.

This free amine 275 mg was treated with HCl gas solved MeOH (2 ml) at room temperature. Then the solvent was evaporated and the residue was solidified from ether by scraching to afford 235 mg of white powder.

Anal. Calcd for $C_{29}H_{32}Cl_2N_2O_5$·HCl·$H_2O$: C,56.73; H, 5.75; N, 4.56. Found: C, 56.51; H, 5.79; N, 4.47.

EXAMPLE 4

17-Cyclopropylmethyl-3,14β-dihydroxy-4,5α-epoxy-6β-(N-methoxy-3,4-dichlorophenylacetamido)morphinan The titled compound was prepared from 17-cyclopropylmethyl-4,5α-epoxy-3,14β-dihydroxy-6β-methoxyaminomorphinan in 76.7% yield according to the procedure similar to that described in example 3.

$^1$H NMR (270 MHz, $CDCl_3$) δ7.41 (1H, br.s), 7.39 (1H, br.d, J=9.5Hz), 7.16 (1H, br.d, J=7.7Hz), 6.71 (1H, br.d, J=7.3Hz), 6.57 (1H, br.d, J=8.1Hz), 4.90 (1H, d, J=8.1Hz), 4.20–4.05 (1H, m), 3.90–3.68 (5H, m, including 3H, br.s, at 3.83 ppm), 3.15–3.06 (1H, m), 3.03 (1H, d, J=18.3Hz), 2.75–2.55 (2H, m), 2.39 (2H, d, J=6.2Hz), 2.38–2.10 (3H, m), 1.70–1.25 (4H, m), 0.90–0.80 (1H, m), 0.60–0.50 (2H, m), 0.20–0.10 (2H, m).

IR(Nujol): 3300, 3250, 1660 $cm^{-1}$.

MS m/z: 562($M^+$+4, 4), 560($M^+$+2, 20), 558($M^+$, 29), 543(6), 527 (4), 412(8), 326(10), 256(10), 210(26), 159(40), 55(100).

This free amine 115 mg was treated with HCl gas solved MeOH (1 ml) at room temperature. Then the solvent was evaporated and the residue was solidified from ether by scraching and recrystalized from MeOH/ether to afford 107 mg of white powder, mp 238°–243°.

Anal. Calcd for $C_{29}H_{32}Cl_2N_2O_5$·HCl·$H_2O$: C,56.73; H, 5.75; N, 4.56. Found: C, 56.36; H, 5.76; N, 4.54.

EXAMPLE 5

17-Cyclopropylmethyl-4,5α-epoxy-14β-hydroxy-3-methoxy-6α-(N-methoxy-3,4-dichlorophenylacetamido)morphinan A mixture of 17-cyclopropylmethyl-3,14β-dihydroxy-4,5α-epoxy-6α-(N-methoxy-3,4-dichlorophenylacetamido)morphinan (197 mg, 0.35 mmol), trimethylsilyldiazomethane (10% solution in $CH_2Cl_2$, 0.57 g, 0.5 mmol), diisopropylethylamine (65 mg, 0.5 mmol), methanol (0.2 ml), and acetonitrile (2 ml) was stirred at room temperature for 13 h. After evaporation of the solvent, the residual oil was purified by preparative thin layer chromatography (1 mm thick plate, $CH_2Cl_2$/MeOH: 10/1) to give 47 mg of amorphous solid. This was purified again by preparative thin layer chromatography (1 mm thick plate, $CH_2Cl_2$/MeOH: 10/1) to give 25 mg of amorphous solid as desired product.

$^1$H NMR (270 MHz, $CDCl_3$) δ7.41 (1H, d, J=2.2Hz), 7.38 (1H, d, J=8.1Hz), 7.16 (1H, dd, J=1.8, 8.1Hz), 6.75 (1H, d, J=8.4Hz), 6.59 (1H, d, J=8.1Hz), 4.90 (1H, td, J=3.7, 13.2Hz), 4.78 (1H, d.J=4Hz), 3.84 (3H, s), 3.83 (1H, d, J=15.4Hz), 3.82 (3H, s), 3.70(1H, d, J=15.8Hz), 3.17 (1H, d, J=6.6Hz), 3.06 (1H, d, J=18.7Hz), 2.75–2.20 (6H, m), 1.88–1.25 (5H, m), 0.95–0.80 (2H, m), 0.60–0.50 (2H, m), 0.20–0.10 (2H, m).

IR(film): 3400, 1660 cm$^{-1}$.

MS m/z: 576(M$^+$+4, 7), 574(M$^+$+2, 36), 572(M$^+$, 50), 545(M$^+$+4-OMe, 8), 543(M$^+$+2-OMe, 34), 541(M$^+$-OMe, 43).

Preparation 7

6-Metoxyiminonaloxone

The titled compound was prepared from naloxone hydrochloride and O-methylhyroxylamine in 95.7% yield according to a procedure similar to that described in preparation 5.

$^1$H NMR (270 MHz, CDCl$_3$) δ6.73 (1H, d, J=8.4Hz), 6.59 (1H, d, J=8.1Hz), 5.88–5.72 (1H, m), 5.27–5.14 (2H, m), 4.97 (1H, s), 3.89 (3H, s), 3.14 (1H,d, J=3.7Hz), 3.10 (1H, d, J=17.2Hz), 2.93 (1H, d, J=6.2Hz), 2.84–2.74 (1H, m), 2.65–2.15 (5H, m), 1.65–1.50 (2H, m), 1.40–1.23 (1H, m).

Preparation 8

17-Allyl-3,14β-dihydroxy-4,5α-epoxy-6α-methoxyaminomorphinan and 17-allyl-3,14β-dihydroxy-4,5α-epoxy-6β-methoxyaminomophinan The titled compounds were prepared from 6-methoxyiminonaloxone in crude 100% yield according to a procedure similar to that described in preparation 6. Purification by silica gel column chromatography (CH$_2$Cl$_2$/MeOH: 30/1 as eluent) afforded 17-allyl-3,14β-dihydroxy-4,5α-epoxy-6α-methoxyaminomorphinan in 48.6% yield as less polar major isomer and 17-allyl-3,14β-dihydroxy-4,5α-epoxy-6β-methoxyaminomorphinan in 17.3% yield as more polar minor isomer and both isomers mixture in 17.5% yield.

6α isomer:
$^1$H NMR (270 MHz, CDCl$_3$) δ6.70 (1H, d, J=8.1Hz), 6.52 (1H, d, J=8.1Hz), 5.81 (1H, tdd, J=6.6, 10.3, 16.9Hz), 5.25–5.13 (2H, m), 4.84 (1H, d, J=3.7Hz), 3.65 (1H, td, J=3.7, 13.2Hz), 3.62 (3H, s), 3.10 (1H, d, J=5.9H 3.08 (1H, d, J=18.7Hz), 2.92 (1H, d, J=6.6Hz), 2.63–2.49 (2H, m), 2.34–2.15 (2H, m), 1.80–1.35 (4H, m), 0.85–0.70 (1H, m).

6β isomer:
$^1$H NMR (270 MHz, CDCl$_3$) δ6.67 (1H, d, J=8.1Hz), 6.57 (1H, d, J=8.1Hz), 5.79 (1H, tdd, J=6.2, 10.3, 17.2Hz), 5.25–5.13 (2H, m), 4.70 (1H, d, J=7.3Hz), 3.64 (3H, s), 3.12 (2H, d, J=6.6Hz), 3.05 (1H, d, J=18.3Hz), 2.89 (1H, d, J=5.5Hz), 2.73–2.49 (3H, m), 2.28–2.02 (3H, m), 1.78–1.57 (2H, m) 1.49–1.25 (2H, m).

EXAMPLE 6

17-Allyl-3,14β-dihydroxy-4,5α-epoxy-6α-(N-methoxy-3,4-dichlorophenylacetamido)morphinan The titled compound was prepared from 6α-methoxyaminonaloxone and 3,4-dichlorophenylacetic acid in 67% yield according to a procedure similar to that described in Example 3.

$^1$H NMR (270 MHz, CDCl$_3$) δ7.44 (1H, d, J=2.2Hz), 7.39 (1H, d, J=8.1Hz), 7.16 (1H, dd, J=2.2, 8.1Hz), 6.71 (1H, d, J=8.1Hz), 6.55 (1H, d, J=8.1Hz), 5.79 (1H, tdd, J=6.6, 10.6, 17.2Hz), 5.25–5.15 (2H, m), 4.85–4.75 (2H, m), 3.82 (1H, d, J=15.4Hz), 3.77 (3H,s), 3.73 (1H, d, J=15.4Hz), 3.15–3.05 (3H, m), 2.92 (1H, d, J=6.6Hz), 2.66–2.50 (2H, m), 2.30–2.15 (2H, m), 1.85–1.35 (5H, m).

IR(Nujol): 3350, 1640 cm$^{-1}$.

MS m/z: 548(M$^+$+4, 5), 546(M$^+$+2, 23), 544(M$^+$, 33), 517(M$^+$+4-OMe, 6), 515(M$^+$+2-OMe, 24), 513(M$^+$-OMe, 30).

This free amine 110 mg was treated with HCl gas solved MeOH (2 ml) at room temperature. Then the solvent was evaporated and the residue was solidified from ethanol/ether by scraching to afford 100 mg of white powder.

Anal. Calcd for C$_{28}$H$_{30}$Cl$_2$N$_2$O$_5$.HCl.2.5H$_2$O: C,53.64; H, 5.79; N, 4.47. Found: C, 53.50; H, 5.58; N, 4.37.

EXAMPLE 7

17-Cyclopropylmethyl-3,14β-dihydroxy-4,5α-epoxy-6α-(N-methoxy-3,4-dichlorobenzamido)morphinan To a solution of 17-cyclopropylmethyl-3,14β-dihydroxy-4,5α-epoxy-6α-methoxy-aminomorphinan (74 mg, 0.2 mmol) and triethylamine (0.07 ml, 0.5 mmol) in CH$_2$Cl$_2$ (5 ml) was added 3,4-dichlorobenzoyl chloride (105 mg, 0.5 mmol) at room temperature. After 0.5 h stirring, the solution was diluted with CH$_2$Cl$_2$ (10 ml), washed with saturated NaHCO$_3$ aqueous solution, dried (Na$_2$SO$_4$), filtered, and concentrated to give 302 mg of white solid. To a solution of this solid in methanol/CH$_2$Cl$_2$ (4 ml/4 ml) was added K$_2$CO$_3$ (28 mg, 0.2 mmol) at room temperature. After 1 h stirring, the solvents were evaporated. To this residue was added saturated NaHCO$_3$ aqueous solution and extracted with CH$_2$Cl$_2$ (10 ml×2). The extract was dried (Na$_2$SO$_4$), filtered, and concentrated to give 201 mg of clear yellow viscous oil, which was purified by preparative TLC (1 mm thick plate×2, CH$_2$Cl$_2$/methanol: 10/1) to give 89 mg (81.7%) of pale yellow viscous oil.

$^1$H NMR (270 MHz, CDCl$_3$) δ7.86 (1H, d, J=1.8Hz), 7.60 (1H, dd, J=1,8, 8.4Hz), 7.49 (1H, d, J=8.4Hz), 6.72 (1H, d, J=8.1Hz), 6.56 (1H, d, J=8.4Hz), 5.00–4.88 (2H, m), 3.51 (3H, s), 3.13 (1H, d, J=6.6Hz), 3.06 (1H, d, J=18.7Hz), 2.70–2.57 (2H, m), 2.44–2.20 (4H, m), 1.90–1.45 (5H, m), 0.95–0.80 (1H, m), 0.60–0.50 (2H, m), 0.16–0.10 (2H, m).

IR(film): 3350, 1630 cm$^{-1}$.

MS m/z: 548(M$^+$+4, 1), 546(M$^+$+2, 6), 544(M$^+$, 8), 517 (M$^+$+4-OMe, 1), 515 (M$^+$+2-OMe, 6), 513(M$^+$-OMe, 8), 346(6), 303(19), 173(29), 55(100).

EXAMPLE 8

17-Cyclopropylmethyl-3,14β-dihydroxy-4,5α-epoxy-6α-(N-methoxy-3,4-dichlorocinnamido)morphinan The titled compound was prepared from 17-cyclopropylmethyl-4,5α-epoxy-3,14β-dihydroxy-6α-methoxyaminomorphinan in 21% yield according to the procedure similar to that described in Example 3.

$^1$H NMR (270 MHz, CDCl$_3$) δ7.65 (1H, d, J=15.8Hz), 7.65 (1H, d, J=2.2Hz), 7.46 (1H, d, J=8.4Hz), 7.38 (1H, dd, J=1.8, 8.4Hz), 7.00 (1H, d, J=15.8Hz), 6.74 (1H, d, J=8.1Hz), 6.56 (1H, d, J=8.4Hz), 5.00–4.88 (2H, m), 3.82 (3H, s), 3.25–3.15 (1H, m), 3.06 (1H, d, J=18.3Hz), 2.80–2.20 (6H, m), 1.90–1.40 (5H, m), 0.95–0.82 (1H, m), 0.60–0.52 (2H, m), 0.20–0.14 (2H, m).

IR(Nujol): 3300, 3250, 1640 cm$^{-1}$.

MS m/z: 574(M$^+$+4, 0.3), 572(M$^+$+2, 1.5), 570(M$^+$, 1.9), 543(M$^+$+4-OMe, 0.6), 541(M$^+$+2-OMe, 2.4), 539(M$^+$-OMe, 3.2), 370(13), 339(16), 310(10), 256(5), 199(12), 55(100).

EXAMPLE 9

17-Allyl-3,14β-dihydroxy-4,5α-epoxy-6β-(N-methoxy-3-furanacrylamido)morphinan The titled compound was prepared from 6β-methoxyaminonaloxone and 3-furanacrylic acid in 10.5% yield according to a procedure similar to that described in Example 3.

$^1$H NMR (270 MHz, CDCl$_3$) δ7.67 (1H, br.s), 7.64 (1H, d, J=15.0Hz), 7.44 (1H, br.s), 6.75 (1H, d, J=8.1Hz), 6.66–6.58 (3H, m, including 1H, d, J=8.1Hz at 6.61 ppm), 5.80–5.60 (1H, m), 5.26–5.13 (2H, m), 4.91 (1H, d, J=8.1Hz), 4.40–4.20 (1H, m), 3.87 (3H, s), 3.14 (2H, d, J=6.2Hz), 3.08 (1H, d, J=18.3Hz), 2.91 (1H, d, J=5.9Hz), 2.70–2.52 (2H, m), 2.40–2.10 (3H, m), 1.75–1.40 (4H, m).

IR(film): 3400, 3250, 1650, 1610 cm$^{-1}$.

MS m/z: 478(M$^+$, 5), 447(M$^+$-OMe, 18), 357(3), 309(3), 242(6), 212(15), 149(8), 121(100).

The chemical structures of the compounds prepared in the Examples 1 to 9 are summarized in the following tables.

TABLE

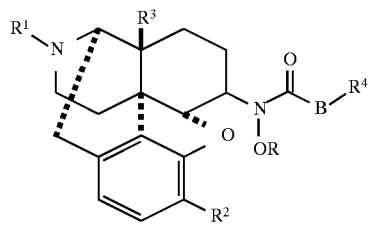

(I)

| Ex. # | R | B | R$^1$ | R$^2$ | R$^3$ | R$^4$ |
|---|---|---|---|---|---|---|
| 1 | H | CH$_2$ | cyclopropylmethyl | OH | OH | 3,4-dichlorophenyl |
| 2 | H | CH$_2$ | cyclopropylmethyl | OH | OH | 3,4-dichlorophenyl |
| 3 | Me | CH$_2$ | cyclopropylmethyl | OH | OH | 3,4-dichlorophenyl |
| 4 | Me | CH$_2$ | cyclopropylmethyl | OH | OH | 3,4-dichlorophenyl |
| 5 | Me | CH$_2$ | cyclopropylmethyl | OMe | OH | 3,4-dichlorophenyl |
| 6 | Me | CH$_2$ | allyl | OH | OH | 3,4-dichlorophenyl |
| 7 | Me | direct bond | cyclopropylmethyl | OH | OH | 3,4-dichlorophenyl |
| 8 | Me | CH=CH | cyclopropylmethyl | OH | OH | 3,4-dichlorophenyl |
| 9 | Me | CH=CH | allyl | OH | OH | furyl |

Note: The stereo chemistry of the compounds of Ex. #1,3,5–8 was 6S. That of Ex. #2,4 and 9 was 6R.

Note: The stereo chemistry of the compounds of Ex. #1, 3, 5–8 was 6S. That of Ex. #2, 4 and 9 was 6R.

I claim:

1. A compound of the following formula:

and the pharmaceutically acceptable salts thereof, wherein
R is hydrogen, C$_1$–C$_5$ alkyl or an O-protecting group;
B is a direct bond, C$_1$–C$_5$ alkylene or C$_2$–C$_5$ alkenylene;
R$^1$ is C$_1$–C$_5$ alkyl, C$_2$–C$_5$ alkenyl or C$_3$–C$_7$ cycloalkyl-C$_1$–C$_3$ alkyl;
R$^2$ is hydroxy or C$_1$–C$_5$ alkoxy;
R$^3$ is hydrogen, hydroxy or C$_1$–C$_5$ alkoxy; and
R$^4$ is hydrogen, phenyl or heteroaryl selected from furyl, thienyl and pyrrolyl, the phenyl and heteroaryl being optionally substituted by one to five substitutents selected from halo, hydroxy, C$_1$–C$_3$ alkyl, C$_1$–C$_3$ alkoxy and C$_2$–C$_5$ alkenyl.

2. A compound according to claim 1, wherein R is hydrogen or C$_1$–C$_5$ alkyl; B is a direct bond, C$_1$–C$_4$ alkylene or C$_2$–C$_4$ alkenylene; R$^1$ is C$_2$–C$_5$ alkenyl or C$_3$–C$_7$ cycloalkyl-C$_1$–C$_3$ alkyl; R$^2$ is hydroxy or C$_1$–C$_3$ alkoxy; R$^3$ is hydrogen, hydroxy or C$_1$–C$_3$ alkoxy; and R$^4$ is phenyl or the heteroaryl, optionally substituted by one to three substitutents selected from halo, hydroxy and C$_1$–C$_3$ alkyl.

3. A compound according to claim 2, wherein R is hydrogen or C$_1$–C$_3$ alkyl; B is a direct bond, C$_1$–C$_3$ alkylene or C$_2$–C$_3$ alkenylene; R$^1$ is C$_2$–C$_3$ alkenyl or C$_3$–C$_5$ cycloalkylmethyl; R$^2$ and R$^3$ are independently hydroxy or C$_1$–C$_3$ alkoxy; and R$^4$ is phenyl, furyl, thienyl or pyrrolyl, optionally substituted by one to three substitutents selected from halo, hydroxy and C$_1$–C$_3$ alkyl.

4. A compound according to claim 3, wherein R is hydrogen, methyl or ethyl; B is methylene, ethylene or ethenylene; R$^1$ is allyl, cyclopropylmethyl, cyclobutylmethyl or cyclopentylmethyl; R$^2$ and R$^3$ are independently hydroxy, methoxy or ethoxy; and R$^4$ is phenyl or furyl, optionally substituted by one to three substitutents selected from fluoro and chloro.

5. A compound according to claim 4, wherein R is hydrogen or methyl; B is methylene or ethenylene; R$^1$ is allyl or cyclopropylmethyl; R$^2$ is hydroxy or methoxy; R$^3$ is hydroxy; and R$^4$ is 3,4-dichlorophenyl or furyl.

6. A compound according to claim 1 selected from

17-Cyclopropylmethyl-3,14β-dihydroxy-4,5α-epoxy-6α-(N-hydroxy-3,4-dichlorophenylacetamido)morphinan or its salts;

17-Cyclopropylmethyl-3,14β-dihydroxy-4,5α-epoxy-6β-(N-methoxy-3,4-dichlorophenylacetamido)morphinan or its salts;

17-Cyclopropylmethyl-3,14β-dihydroxy-4,5α-epoxy-6α-(N-methoxy-3,4-dichlorophenylacetamido)morphinan or its salts;

17-Cyclopropylmethyl-3,14β-dihydroxy-4,5α-epoxy-6β-(N-methoxy-3,4-dichlorophenylacetamido)morphinan or its salts;

17-Cyclopropylmethyl-4,5α-epoxy-14β-hydroxy-3-methoxy-6α-(N-methoxy-3,4-dichlorophenylacetamido) morphinan or its salts;

17-Allyl-3,14β-dihydroxy-4,5α-epoxy-6α-(N-methoxy-3,4-dichlorophenylacetamido) morphinan or its salts;

17-Cyclopropyl methyl-3,14β-dihydroxy-4,5α-epoxy-6α-(N-methoxy-3,4-dichlorobenzamido)morphinan or its salts;

17-Cyclopropylmethyl-3,14β-dihydroxy-4,5α-epoxy-6α-(N-methoxy-3,4-dichlorocinnamido)morphinan or its salts; and 17-Allyl-3,14β-dihydroxy-4,5α-epoxy-6β-(N-methoxy-3-furanacrylamido)morphinan or its salts.

7. A compound according to claim 6 selected from 17-Cyclopropylmethyl-3,14β-dihydroxy-4,5α-epoxy-6α-(N-hydroxy-3,4-dichlorophenylacetamido)morphinan or its salts; and 17-Cyclopropylmethyl-3,14β-dihydroxy-4,5α-epoxy-6α-(N-methoxy-3,4-dichlorophenylacetamido)morphinan or its salts.

8. A pharmaceutical composition comprising an amount of a compound according to claim 1 effective as an analgesic and a pharmaceutically acceptable carrier.

9. A method for alleviating or treating pain in a mammalian subject, which comprises administering to said afflicted subject a therapeutically-effective analgesic amount of a compound according to claim 1.

* * * * *